United States Patent [19]

Ljungstroem

[11] Patent Number: 5,095,902
[45] Date of Patent: Mar. 17, 1992

[54] IMPLANTABLE MEDICAL STIMULATION SYSTEM OPTIONALLY OPERABLE IN A BIPOLAR OR A UNIPOLAR MODE

[75] Inventor: Jan Ljungstroem, Solna, Sweden

[73] Assignee: Siemens Aktiengesellschaft, Berlin and Munich, Fed. Rep. of Germany

[21] Appl. No.: 572,416

[22] Filed: Aug. 27, 1990

[30] Foreign Application Priority Data

Aug. 28, 1989 [EP] European Pat. Off. ........ 89115851.1

[51] Int. Cl.$^5$ .............................................. A61N 1/36
[52] U.S. Cl. ........................... 128/419 PG; 128/419 P
[58] Field of Search ........................ 128/419 PG, 419 P

[56] References Cited

U.S. PATENT DOCUMENTS

| | | | |
|---|---|---|---|
| 4,236,525 | 12/1980 | Sluetz et al. ..................... | 128/419 P |
| 4,301,805 | 11/1981 | Peer-Trevarton et al. ...... | 128/419 P |
| 4,420,216 | 12/1983 | Motoyama et al. . | |
| 4,532,931 | 8/1985 | Mills .............................. | 128/419 PG |
| 4,558,702 | 12/1985 | Barreras et al. ............... | 128/419 PG |
| 4,741,342 | 5/1988 | Stotts ............................. | 128/419 PG |

*Primary Examiner*—William E. Kamm
*Assistant Examiner*—Kennedy J. Schaetzle
*Attorney, Agent, or Firm*—Hill, Van Santen, Steadman & Simpson

[57] ABSTRACT

An implantable medical stimulation system optionally operable in a bipolar or a unipolar mode includes a stimulation device and a bipolar electrode and a unipolar electrode optionally electrically connectable thereto. The electrodes conduct electrical signals between the stimulation device and the body of a patient in whom the system is implanted. The connection located at the stimulation device for the electrodes has a terminal carrying a signal potential and a terminal carrying a reference potential. When the device is switched for unipolar operation, the terminal carrying the reference potential is connected so that reference potential is supplied to the body of the patient by some means other than the unipolar electrode. To avoid danger to the patient if the device is errroneously switched for operation in the bipolar mode when the unipolar electrode is connected, the unipolar electrode and the connector on the stimulation device in combination provide a nonswitchable connection to the other means for applying the reference potential.

9 Claims, 1 Drawing Sheet

IMPLANTABLE MEDICAL STIMULATION SYSTEM OPTIONALLY OPERABLE IN A BIPOLAR OR A UNIPOLAR MODE

BACKGROUND OF THE INVENTION

1. Field of the Invention

The present invention is directed to an implantable medical stimulation system of the type which is optionally operable in a bipolar mode or in a unipolar mode, and in particular to such a device having a connector adapted to receive a bipolar lead or a unipolar lead, depending upon the intended mode of operation.

2. Description of the Prior Art

Medical stimulation devices, such as heart pacemakers, are known in the art which can be optionally operated in a bipolar mode or in a unipolar mode. When employing a unipolar electrode, a body region of the patient in whom the system is implanted is connected by the unipolar electrode to a terminal within the stimulation device which carries the signal potential, so that electrical signals can be conveyed via the electrode to and from the body region. The reference potential is applied at a different location of the body of the patient by a separate means for applying the reference potential. A unipolar electrode therefore usually has only one conductor.

When a bipolar electrode is employed, both the terminal carrying the signal and the terminal carrying the reference potential, at the stimulation device, are connected by the bipolar electrode to a region of the body to which and from which electrical signals are conveyed. A bipolar electrode therefore contains two conductors, each of which terminate in exposed contacts which are relatively close to each other, and which are adapted to make an electrical connection with the body region. It is thus possible to operate the device in a unipolar fashion using a bipolar electrode, by connecting only one conductor of the bipolar electrode to the terminal of the device which carries the signal potential. The reference potential is then applied to the body of the patient in some other way. It is, of course, not possible to operate the device in a bipolar fashion using a unipolar electrode.

Systems of the type described above are known in the art wherein the stimulation device is a heart pacemaker, and the electrodes lead from the heart pacemaker to the patient's heart. The pacemaker includes means for stimulating heart activity and means for detecting heart beats. Stimulation pulses from the means for stimulating are conducted to the heart via an electrode, and signals corresponding to the electrical activity of the heart are also conducted via the electrode to the means for detecting in the pacemaker. Such known pacemakers are implantable in the body of a patient with a unipolar or a bipolar endocardial electrode connected thereto at the time of implantation. The electrode is conducted through the vein system of the patient to the appropriate atrium or ventricle of the heart, and is anchored therein. Under some circumstances, it may be desirable after implantation of the system to switch from bipolar to unipolar operation and vice versa. Such switching can ensue telemetrically using an external device, known as a programmer. It is, of course, a prerequisite to such switching that the system be implanted with a bipolar electrode, if operation in the bipolar mode is desired as an option.

Switching from bipolar stimulation to unipolar stimulation, for example, may be desired because the amount of energy required for achieving a stimulation is lower in most patients for unipolar stimulation. Switching from unipolar to bipolar stimulation is necessary when undesirable stimulation side-effects, for example muscle tics, appear in the body region at which the reference potential is applied. In the case of a heart pacemaker, this will normally be in the region of the electrically conductive housing of the pacemaker, which is electrically connected to the terminal of the device carrying the reference potential. A switch from unipolar to bipolar detection can be useful if substantial noise is present given unipolar detection. Such noise is usually less pronounced given bipolar detection. Whereas switching from bipolar to unipolar operation does not pose significant problems, switching from unipolar to bipolar operation, particularly after implantation of the system has already been undertaken, makes it necessary that the attending physical be sure that a bipolar electrode is in fact connected to the heart pacemaker. In the event of a mistake, proper stimulation is no longer insured, and thus life-threatening situations may arise for patients who are completely dependent on the artificial stimulation by the heart pacemaker, or are dependent thereon to a substantial degree.

SUMMARY OF THE INVENTION

It is an object of the present invention to provide an implantable medical stimulation device optionally operable in a bipolar mode or a unipolar mode wherein it is insured that switching from a unipolar to a bipolar mode of operation will pose no danger to the patient.

The above object is achieved in an implantable medical system wherein, given connection of a unipolar electrode to the stimulation device, an electrical connection of the terminal carrying the reference potential to the means for applying the reference potential will always be present, regardless of the switching state of the device. This means that a connection between the terminal carrying the reference potential and the means for applying the reference potential will be present even when a unipolar electrode is connected to the device and a switch is undertaken to bipolar operation, under the mistaken assumption that a bipolar electrode is connected. Malfunctions and potential life-threatening consequences for the patient are thus reliably avoided.

The stimulation device may include electrical connecting means which permit optional connection of a bipolar electrode or a unipolar electrode to the device, with the electrical connecting means operating in combination with the unipolar electrode so that a connection of the terminal which carries the reference potential to the means for applying the reference potential is necessarily present given connection of the unipolar electrode. Electrical connecting means which are already necessary for the connection of an electrode can thus be modified so that the desired conductive connection necessarily occurs given connection of a unipolar electrode, so that the required technical outlay is extremely low.

In a preferred embodiment of the invention, the electrical connection means is a plug-type connector having a first connector part allocated to the stimulation device having at least two poles. A first pole is connected to the terminal carrying the signal potential and a second pole is connected to the terminal carrying the reference potential for bipolar operation. A second connector part allocated to the bipolar electrode, also has at least two poles. The two poles of the second connector part respectively are in electrical contact with the poles of the first connector part given connection of the bipolar electrode. A unipolar electrode has a second connector part having one pole, the one pole of the second connector part of the unipolar electrode making electrical contact with the first pole of the first connector part of the stimulation device given connection of the unipolar electrode. The second connector part of the unipolar electrode includes means which necessarily make a conductive connection between the second pole of the first connector part and the means for applying the reference potential, when the pole of the second connector part allocated to the unipolar electrode is in contact with the first pole of the first connector part.

A plug connector forming the second connector part of the unipolar electrode is therefore fashioned so that the desired conductive connection between the terminal of the device carrying the reference potential and the means for applying the reference potential occurs as a necessary result of the insertion of the unipolar electrode plug in the first connector part of the stimulation device.

In a modification of the invention, the first connector part may include a third pole which is electrically connected to the means for applying the reference potential, and the second connector part of the unipolar electrode produces a conductive connection between the second and third poles of the first connector part when inserted. This connection can be produced by a contact piece attached to the second connector part of the unipolar electrode.

In a further embodiment, the plug connector may be a coaxial, rotationally symmetrical plug connector which can be manufactured in a technologically simple and economical way with the poles of the first connector part of the stimulation device being arranged in axial succession and the second and third poles being adjacent to each other.

The invention disclosed herein has particular advantage when incorporated in a device implantable into the body of a patient which is telemetrically switchable from unipolar to bipolar operation. In such a device, it is especially difficult after implantation to recognize whether a bipolar electrode is in fact connected to the device, so that a mistaken switching to bipolar operation can occur relatively easily, and prevention of the aforementioned negative consequences for the patient is especially important.

DESCRIPTION OF THE PREFERRED EMBODIMENTS

Figure 1:
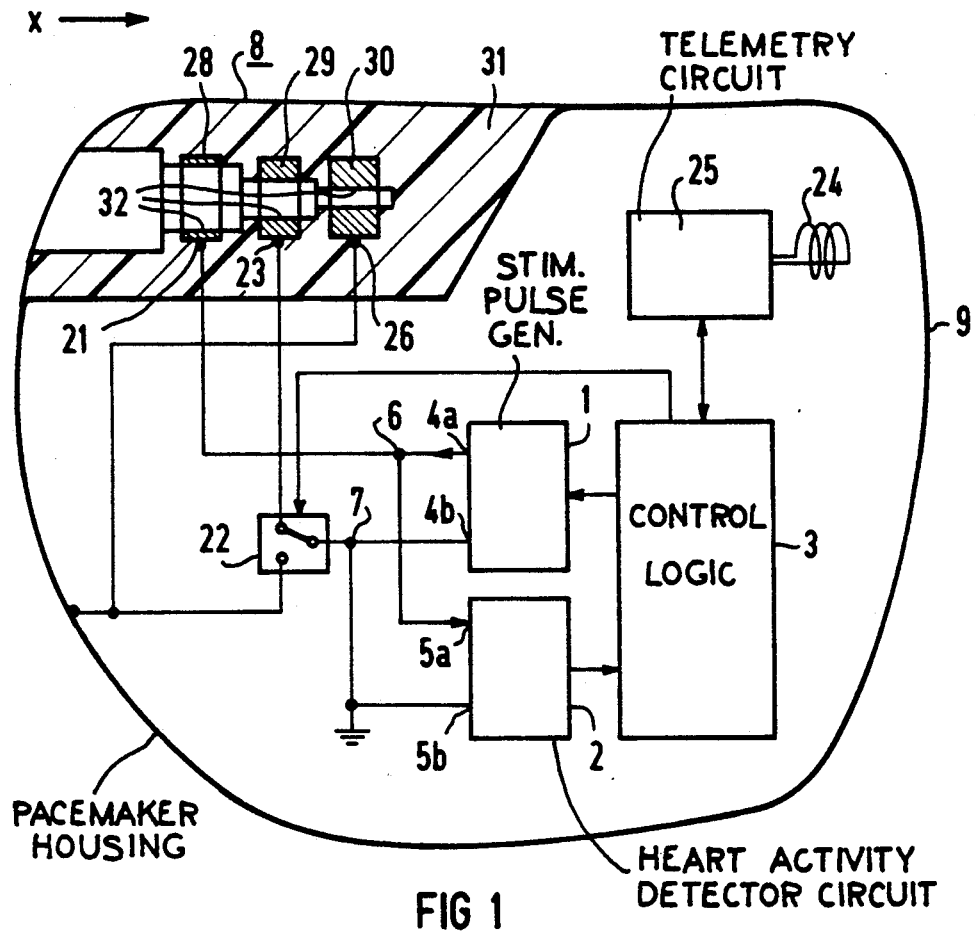
FIG. 1 is a side sectional view of a heart pacemaker constructed in accordance with the principles of the present invention, with relevant electrical components shown in a schematic block diagram.

A heart pacemaker constructed in accordance with the principles of the present invention includes a stimulation pulse generator 1 and a heart activity detector circuit 2, each of which is respectively connected to control logic 3. The control logic 3 always initiates the stimulation pulse generator 1 to generate an electrical stimulation pulse if the detector circuit 2 has not detected a natural heartbeat before a time interval corresponding to a specific heartbeat rate has elapsed, following a natural heartbeat detected by the detector circuit 2 or following a stimulation pulse generated by the stimulation pulse generator 1. The stimulation pulse generator 1 has an output 4a which carries the stimulation potential, and has an output terminal 4b which carries a reference potential.

The detector circuit 2 has an input 5a at which the potential corresponding to the electrical activity of the heart is present, and an input terminal 5b which carries the reference potential.

Conduction of the stimulation pulses from the stimulation pulse generator 1 to the heart, and the conduction of the signals corresponding to the electrical activity of the heart to the detector circuit 2 takes place via a common lead. For this purpose, therefore, the output 4a of the stimulation pulse generator 1 is connected to the input 5a of the detector circuit 2, and the output terminal 4b of the stimulation pulse generator 1 is connected to the input terminal 5b of the detector circuit 2.

The pacemaker has a terminal 6 which carries the signal potential which is formed by the junction of the output 4a of the stimulation pulse generator 1 and the output 5a of the detector circuit 2. The pacemaker also has a terminal 7 carrying the reference potential which is formed by the junction of the output terminal 4b of the stimulation pulse generator 1 and the input terminal 5b of the detector circuit 2.

An electrode (not shown in FIG. 1) provides the conductive connection between the terminal 6 which carries the signal potential and the heart of the patient. The terminal 6 is therefore connected to a first pole 21 of a plug connector which is adapted to receive both bipolar and unipolar electrodes. The plug connector consists of first and second mating components, with only the first connector part 8, allocated to the heart pacemaker, being shown in FIG. 1.

If a bipolar electrode is used, the reference potential is applied directly to the heart via the bipolar electrode. The first connector part 8 therefore has a second pole 23 connectable to the terminal 7 which carries the reference potential. This connection can take place via a switch 22, which may be an electronic switch. The switch 22 is shown in FIG. 1 in a state for bipolar operation. If a unipolar electrode is used, by contrast, the reference potential is applied to the body of the patient via a hermetically tight housing 9 (schematically indicated in FIG. 1), which contains the electronic components of the pacemaker and consists of an electrically conductive material, for example titanium. For unipolar operation, the switch 22 changes state to its other switch position, so that an electrical connection is present between the terminal 7 which carries the reference potential and the housing 9.

The first connector part 8 of the plug connector, which is allocated to the pacemaker, is secured to the housing 9.

Figure 2:
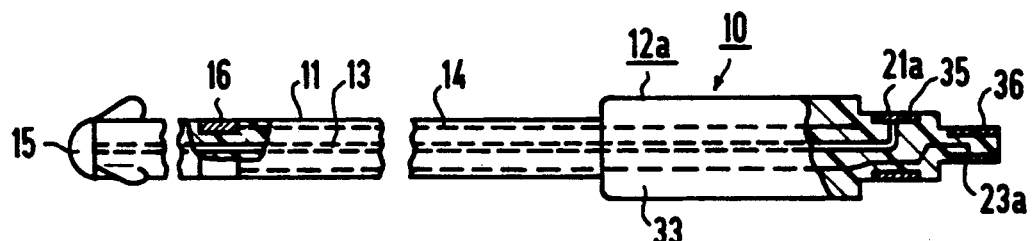
FIG. 2 is a side view, partly broken away, of a bipolar electrode constructed in accordance with the principles of the present invention for connection to the pacemaker of FIG. 1.

A bipolar electrode 10 is shown in FIG. 2 which includes a two-pole line 11 and a second connector part 12a of the plug connector. The second connector part 12a is introducible into the first connector part 8 attached to the pacemaker. The line 11 has an inner conductor 13 and an outer conductor 14. The outer conductor 14 may be, for example, metal braid surrounding the inner conductor 13 and electrically insulated therefrom. The outer conductor 14 is also insulated. The inner conductor 13 is electrically connected to a tip 15 which is brought into contact with part tissue to be stimulated. The inner conductor 13 supplies stimulation pulses to the heart, and also supplies the pacemaker with signals from the heart corresponding to the electrical activity of the heart. The outer conductor 14 is electrically connected to a ring 16, which is also brought into contact with heart tissue, and which serves the purpose of placing the heart at the reference potential.

Figure 3:
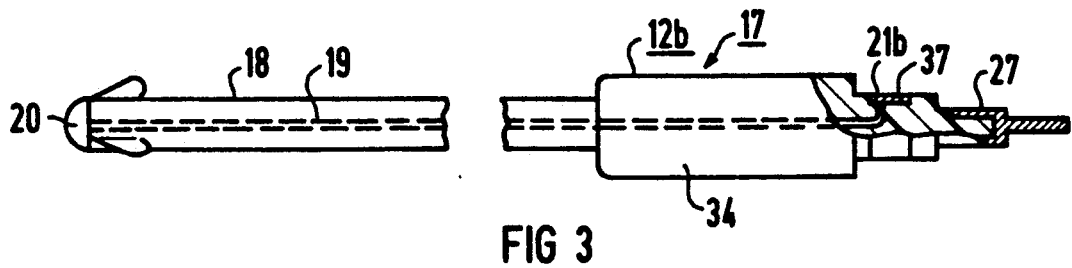
FIG. 3 is a side view, partly broken away, of a unipolar electrode constructed in accordance with the principles of the present invention, for connection to the pacemaker of FIG. 1.

A unipolar electrode 17 is shown in FIG. 3. The unipolar electrode 17 has a single pole line 18 having a conductor which terminates in the tip 20 and which conducts stimulation pulses to the heart and conveys electrical signals from the heart corresponding to the heart electrical activity. The unipolar electrode 17 also has a second connector part 12b which is insertable in the first connector part 8 of the pacemaker. When the unipolar electrode 17 is used, as was stated above, the reference potential is not applied directly to the heart, but is applied to the body of the patient via the electrically conductive housing 9 (see FIG. 1) of the pacemaker.

As can also be seen in FIG. 2, the second connector part 12a has a first pole 21a and a second pole 23a. When the second connector part 12a is inserted in the first connector part 8, the poles 21a and 23a will be in registry with the poles 21 and 23 and will be in electrical contact therewith so that the tip 15 will be at the signal potential via the inner conductor 13, and the ring 16 will be at the reference potential via the outer conductor 14. As can be seen in FIG. 3, the second connector part 12b of the unipolar electrode has a first pole 21b which will be in registry with the first pole 21 of the first connector part 8 when the second connector part 12b is inserted therein. The tip 20 will thus be at the signal potential via the conductor 19.

Therefore, if the bipolar electrode 10 is connected to the pacemaker, stimulation and detection can be optionally undertaken in a bipolar mode or in a unipolar mode, dependent on the state of the switch 22. The switch position of the switch 22 shown in FIG. 1 corresponds to the bipolar mode, as described above.

The pacemaker shown in FIG. 1 also includes a telemetry circuit 25 connected to a transmission/reception coil 24. The telemetry circuit 25 is connected to the control logic 3. An external programmer (not shown), which also includes a transmission/reception coil and a telemetry circuit, permits data to be exchanged between the pacemaker and the external programmer, even after implantation. This is accomplished by bringing the transmission/reception coil of the external device into proximity with the transmission/reception coil 24 of the implanted pacemaker, so that an inductive coupling between the coils is achieved. Among other things, it is possible to telemetrically actuate the switch 22, as indicated by a control line between the switch 22 and the control logic 3, to switch the pacemaker from bipolar to unipolar operation, and vice versa.

There is no problem when a bipolar electrode 10 is connected to the pacemaker, because this electrode can be employed for unipolar stimulation and detection as well. If, however, a unipolar electrode 17 is connected, and the pacemaker is mistakenly switched to bipolar operation, malfunctions and danger to the patient can arise, as explained above.

To prevent these malfunctions and to ensure patient safety given the connection of a unipolar electrode 17, the first connector part 8 includes a third pole 26 which is permanently electrically connected to the housing 9 of the pacemaker. The second connector part 12b of the unipolar electrode 17 has a contact piece 27 fashioned to produce an electrical connection between the third pole 26 and the second pole 23 of the first connector part 8 when a unipolar electrode 17 is inserted. Regardless of the state of the switch 22, an electrical connection between the terminal 7 which carries the reference potential and the housing 9 of the pacemaker will exist when a unipolar electrode 17 is connected. Malfunctions and danger to the patient thus do not arise if the heart pacemaker is mistakenly switched to bipolar operation with a connected unipolar electrode 17.

As can be seen in FIGS. 1 through 3, the plug connection is preferably a coaxial, rotationally-symmetrical plug connector. The poles of the first connector part 8 are formed by three annular contacts 28, 29 and 30 disposed axially spaced from each other. insulating material and having a bore 32 for acceptance of the second connector part 12a or 12b. The exposed surfaces of the contacts 28, 29 and 30 form portions of the wall of the bore 32. The bore diameters of the contact parts 28, 29 and 30 decrease in the insertion direction, indicated by an arrow x. The contact 28 forms the first pole, the contact 29 forms the second pole, and the contact 30 forms the third pole of the first connector part 8.

The second connector parts 12a and 12b are respectively formed by base members 33 or 34, consisting of electrically insulating material. The base members 33 and 34 are shaped so as to be introduced into the bore 32 of the first connector part 8. In the case of the second connector part 12a of the bipolar electrode 10, the two poles thereof are formed by annular contacts 35 and 36. The contacts 35 and 36 have exposed cylindrical surfaces forming the contact surfaces, and engage the respective contacts 28 and 29 of the first connector part 8 when the second connector part 12a is plugged therein.

The single pole of the connector part 12b of the unipolar electrode 17 is formed by a contact 37 which corresponds to the contact 35 in terms of dimensions and location. The second connector part 12b also has a contact 27, as noted above, arranged and shaped so that when the second connector part 12b is inserted in the first connector part 8, the contact 27 bridges the contacts 29 and 30 so that an electrical connection exists between the contacts 29 and 30.

Although modifications and changes may be suggested by those skilled in the art, it is the intention of the inventor to embody within the patent warranted hereon all changes and modifications as reasonably and properly come within the scope of his contribution to the art.

I claim as my invention:

1. An implantable system for stimulating body tissue of a patient, comprising:
   a stimulation device optionally operable in a unipolar mode or in a bipolar mode, said device having a first terminal carrying a reference potential and a second terminal carrying a signal potential;

means, when said stimulation device is in said unipolar mode, for applying said reference potential to said body tissue; said stimulation device further comprising a third terminal connected to said means for applying said reference potential;

a unipolar electrode connectable to said stimulation device at said first and second terminals; and means for automatically making a non-switchable connection between said first terminal and said means for applying reference potential when said unipolar electrode is connected to said stimulation device.

2. An implantable system as claimed in claim 1 wherein said stimulation device and said unipolar electrode have mating electrical connection elements, and wherein said means for automatically making a non-switchable connection is carried on the electrical connection element of said unipolar electrode.

3. An implantable system as claimed in claim 1 further comprising:

a plug receptacle in said stimulation device in which said first and second terminals are disposed;

a bipolar electrode having a plug element having first and second poles which respectively make electrical contact with said first and second terminals when said plug element of said bipolar electrode is inserted in said plug receptacle; and a plug element on said unipolar electrode having a single pole which makes electrical contact with said first terminal when said plug element of said unipolar electrode is inserted in said plug receptacle, and wherein said means for automatically making a non-switchable connection are carried on said plug element of said unipolar electrode.

4. An implantable system as claimed in claim 3 wherein said third terminal 15 disposed in said plug receptacle, and wherein said means for automatically making a non-switchable connection is means carried on said plug element of said unipolar electrode for automatically making an electrical connection between said second and third terminals when said plug element of said unipolar electrode is inserted in said plug receptacle.

5. An implantable system as claimed in claim 4 wherein said means for automatically connecting said second and third terminals is a contact piece carried on said plug element of said unipolar electrode which bridges said second and third terminals when said plug element of said unipolar electrode is inserted in said plug receptacle.

6. An implantable system as claimed in claim 5 wherein each of said plug elements of said bipolar electrode and said unipolar electrode are respective coaxial, rotationally-symmetrical plug connectors, and wherein said first, second and third terminals are disposed in said plug receptacle in spaced axial succession, with said second and third terminals being adjacent each other.

7. An implantable system as claimed in claim 1 further comprising means for telemetrically switching said stimulation device for operation in said unipolar mode or in said bipolar mode.

8. An implantable system as claimed in claim 1 wherein said means for applying said reference potential to said body tissue is a housing of said stimulation device.

9. An implantable system as claimed in claim 1 wherein said stimulation device is a heart pacemaker, including means for stimulating heart activity and means for detecting electrical heart activity via said unipolar electrode in said unipolar mode and via a bipolar electrode in said bipolar mode.

* * * * *